(12) United States Patent
Peng et al.

(10) Patent No.: US 8,828,239 B2
(45) Date of Patent: *Sep. 9, 2014

(54) FLEXIBLE FREE-STANDING ULTRATHIN OR THIN PROTEIN MEMBRANE, ITS FABRICATION METHOD AND APPLICATION

(75) Inventors: XinShen Peng, Tsukuba (JP); Izumi Ichinose, Tsukuba (JP)

(73) Assignee: National Institute for Materials Science, Tsukuba-shi, Ibaraki (JP)

(*) Notice: Subject to any disclaimer, the term of this patent is extended or adjusted under 35 U.S.C. 154(b) by 707 days.

This patent is subject to a terminal disclaimer.

(21) Appl. No.: 12/654,931

(22) Filed: Jan. 8, 2010

(65) Prior Publication Data
US 2010/0140163 A1 Jun. 10, 2010

Related U.S. Application Data

(63) Continuation of application No. PCT/JP2008/062979, filed on Jul. 11, 2008.

(30) Foreign Application Priority Data

Jul. 11, 2007 (JP) ................................. 2007-181832
Nov. 8, 2007 (JP) ................................. 2007-290238

(51) Int. Cl.
*B82Y 5/00* (2011.01)
*B01D 67/00* (2006.01)
*B01D 71/74* (2006.01)
*B01D 69/12* (2006.01)
*B01D 69/14* (2006.01)

(52) U.S. Cl.
CPC .................. *B01D 69/122* (2013.01); *B82Y 5/00* (2013.01); *B01D 2323/30* (2013.01); *B01D 67/0006* (2013.01); *B01D 71/74* (2013.01); *B01D 69/144* (2013.01); *Y10S 977/705* (2013.01); *Y10S 977/84* (2013.01); *Y10S 977/89* (2013.01)
USPC ........... 210/702; 977/705; 977/840; 977/890; 524/17

(58) Field of Classification Search
None
See application file for complete search history.

(56) References Cited

U.S. PATENT DOCUMENTS

2004/0049230 A1   3/2004   Montemagno et al.
2004/0242714 A1  12/2004   Penezina et al.

FOREIGN PATENT DOCUMENTS

| JP | S63-300770 | 12/1984 |
|---|---|---|
| JP | S-61-291994 | 12/1986 |
| JP | H02-236153 | 9/1990 |
| JP | 2005-274141 | 10/2005 |
| JP | 2006-000929 | 1/2006 |
| WO | WO2007/037315 | 4/2007 |

OTHER PUBLICATIONS

Gerl et al. Mechanism of the self-assembly of apoferritin from horse spleen. Eur Biophys J (1987) 15: 103-109.*

(Continued)

*Primary Examiner* — Katherine Zalasky
(74) *Attorney, Agent, or Firm* — Manabu Kanesaka (57) ABSTRACT

A fabrication method for a flexible porous free-standing protein membrane formed by cross-linked protein includes (1) mixing nanostructured materials and protein to obtain a composite made of protein and nanostructured materials (for example metal hydroxide nanostrands); (2) forming a membranous body formed by the composite made of protein and nanostructured materials, and mutually cross-linking the protein by a cross-linker; and (3) dissolving and removing the nanostructured materials to produce a flexible porous freestanding protein membrane.

8 Claims, 8 Drawing Sheets

(56) References Cited

OTHER PUBLICATIONS

Peng et al. Mesoporous separation membranes of polymer-coated copper hydroxide nanostrands. Adv. Funct. Mater. (2007) 17: 1849-1855.*

Peng et al. General method for ultrathin free-standing films of nanofibrous composite materials. J. Am. Chem. Soc. (2007) 129: 8625-8633.*

European Patent Office, "Supplementary European Search Report for EP 08778271.0", Oct. 4, 2011.

European Patent Office, "European Examination Report for EP 08778271.0", Jul. 6, 2012.

Shitij Chabba et al., "'Green' Composites Part 1: Characterization of Flax Fabric and . . . ", Journal of Materials Science 40 (2005), Dec. 1, 2005, pp. 6263-6273.

Claudia M. Vaz et al., "Effect of Crosslinking, Thermal Treatment and UV Irradiation . . . ", Journal of Materials Science:Materials in Medicine, 14, No9, Jan. 1, 2003, 789-796.

Izumi Ichinose et al., "Electrostatic Trapping of Double-Standard DNA by Using Cadium Hydroxide Nanostrands", Nano Letters, vol. 5, No. 1, Jan. 1, 2005, pp. 97-100.

Svobodov L. et al., "Properties of Glucose Biosensors based on Dendrimer Layers . . . ", Analytical and Bioanalytical Chemistry, vol. 373, No. 8, Aug. 1, 2002, pp. 735-741.

* cited by examiner

FLEXIBLE FREE-STANDING ULTRATHIN OR THIN PROTEIN MEMBRANE, ITS FABRICATION METHOD AND APPLICATION

ART FILED

This invention relates to a flexible free-standing ultrathin (nano) or thin protein membrane which enables a rapid and simple separation (or condensation) of relatively small (M.W. ca. 1,000) molecules as well as large molecules. This invention also relates to a fabrication method of the above protein membrane and relates applications of the above protein membrane.

BACKGROUND OF THE INVENTION

Today, membranes are widely and practically applied to produce potable water from sea, to clean industrial effluents and recover valuable constituents, to concentrate, purify or fractionate macromolecular mixtures in the food and drug industries, and to separate gases and vapors. They are also key components in energy conversation systems, and in artificial organs and drug delivery devices. Their widespread use in separations has, however, been limited by the difficulty of preparing membranes with the desirable combination of high selectivity, which yields high product purity and low operating costs, and high permeability, which reduces membrane area and capital cost, as well as the high membrane flux. Thus high membrane flux is the key performance criterion that determines the cost of a membrane system. Unfortunately, as the selectivity of conventional polymer membrane materials increases, permeability invariably decreases and vice versa; and as decreasing the thickness to increase the flux, the stability dramatically decreased. Attempts to overcome the first fundamental limitation have explored the addition of micron-sized porous zeolite particles to organic polymers in the hope of combining the mechanical elasticity and processability of polymers with the strong size selectivity characteristic of spatially well-defined zeolite pores (Lai, Z. P. et al, 2003). Commercialization of this approach, however, has been hampered by poor polymer/zeolite adhesion, inadequate particle dispersion and low membrane flux.

The developing of new nanostructured materials with specific configurations and morphology is offering powerful tools for the preparation of membranes with highly controllable selectivity and permeability for gas separation (Lai, Z. P. et al, 2003; De Vos, R. M. et al, 1998; Merekel, T. C. et al, 2002; Shiflett, M. B. et al, 1999). Up to date, nanocomposite membranes are almost keep the thickness more than hundred nanometers and with support layer, which significantly limit the membrane flux, separation efficiency and macroscale application, especially, for liquid separation system (Holt, J. K. et al, 2006; Jirage, K. B. et al, 1997). Even several ultrathin (several tens nanometers thick) free-standing films were reported (Yang, H. et al, 1996; Mamedov, A. A. et al, 2002; others), and used for sensors and actuators, but without any report about their separation performance because of the lack of the functional designation and workability, except that the first example for using ultrathin nanomembranes for size-based macromolecular separation was carried out by Striemer' and coworkers by using 15 nm thick free-standing silicon membranes prepared by using precision deposition of silicon and etching techniques and thermal annealing process at high temperature (above 700° C.) (Striemer. C. C. et al, 2007).

In our laboratory, we developed a general method to synthesize macroscale ultrathin free-standing mesoporous films with fibrous nanocomposite of negatively charged dye molecules (see non-patent ref. 1), DNA (see non-patent ref. 2), and positively charged metal hydroxide nanostrands (see non-patent ref. 3, non-patent ref. 4) by a simple filtration and peeling off techniques. Unfortunately, these fibrous nanocomposite films were fragile and easily destroyed due to the weak chemical stability of metal hydroxide nanostrands. Therefore, conjugated polymers (polyaniline, polypyrrole) was coated on nanostrands and formed mesoporous thin films for size selective separation of proteins in physiological conditions (Peng, X. S. et al, 2007). However, such film still can not be sustained in the solution with pH lower than 4.

[Non-Patent Ref. 1]
Luo, Y.-H., Huang, J., Ichinose, I. "Bundle-like assemblies of cadmium hydroxide nanostrands and anionic dyes" *J. Am. Chem. Soc.* 127, 8296-8297 (2005).

[Non-Patent Ref. 2]
Ichinose, I., Huang, J., Lou, Y.-H. "Electrostatic trapping of double-strand DNA by using cadmium hydroxide nanostrands" *Nano Lett.* 5, 97-100 (2005).

[Non-Patent Ref. 3]
Ichinose, I., Kurashima, K., Kunitake. T. "Spontaneous formation of cadmium hydroxide nanostrands in water" *J. Am. Chem. Soc.* 126, 7162-7163 (2004).

[Non-Patent Ref. 4]
Luo, Y.-H. et al. "Formation of positively charged copper hydroxide nanostrands and their structural characterization" *Chem. Mater.* 18, 1795-1782 (2006)

DISCLOSURE OF THE INVENTION

Problems to be Solved by the Invention

In order to solve the above problems of the fibrous nanocomposite films, we have further studied the coating of positively charged metal hydroxide nanostrands with proteins. And fortunately we have succeeded in developing a robust and flexible free-standing ultrathin (nano) or thin pure protein membrane by covalently cross-linking the proteins in the fibrous composite films by glutaraldehyde (GA) and removing away the inorganic nanostrands.

Measures for Overcoming the Problems

Namely, this invention provides a porous free-standing protein membrane formed by cross-liked protein, characterized in that at least part of the pores of said porous membrane were formed by removing nanostructured materials. Here, "membrane" is synonymous with "film", and "free-standing" is synonymous with "self-supporting" in this specification. Said nanostructured materials are preferably nanostrands.

This invention also provides a fabrication method for a porous free-standing protein membrane formed by cross-liked protein, whose method comprises the following steps:
(1) a first step of mixing nanostructured materials and protein to obtain composite made of protein and nanostructured materials;
(2) a second step of forming a membranous body formed by said composite made of protein and nanostructured materials, and mutually cross-linking said protein by means of a cross-linker; and
(3) a third step of dissolving and removing said nanostructured materials to produce a porous membrane.

In said fabrication method for a porous free-standing protein membrane, said nanostructured materials are preferably metal hydroxide nanostrands, and said membranous body is preferably formed by assembling composite nanofibers made of protein and said metal hydroxide nanostrands.

This invention also provides some applications of the above porous free-standing protein membrane. As one application, this invention provides a composite protein membrane formed by integrating a protein membrane and another molecular membrane, characterized in that said protein membrane is above porous free-standing protein membrane.

In said composite protein membrane, said molecular membrane and said protein membrane are preferably cross-linked by means of a cross-linker for integration.

Effect of the Invention

The invented porous free-standing protein membrane formed by cross-liked protein is thin and novel. In some case (using apoferritin as protein), the obtained protein membranes showed the films with homogenous thickness of 25 nm, and diameter of 7.5 cm, with the ratio of diameter to thickness up to 3,000,000 (Such high ratio was not reported before).

The invented porous free-standing thin protein membrane can be applied for size selective separation of molecules having small molecular weight (ca. 1000 or less than 1000). They can be also applied for pH controlling separation of molecules with high efficiency, and pH trigging, reversible adsorption and desorption of dye molecules with very high capacitance of molar ratio.

According to the invented fabrication method, we can easily fabricate a porous free-standing thin protein membrane formed by cross-liked protein.

The invented free-standing thin film composed of two layers, one of which is the above porous free-standing thin protein membrane, the other one is a thin molecular membrane are novel multilayer films, and therefore they may be used differently from the invented porous free-standing thin protein membrane.

Figure 9:
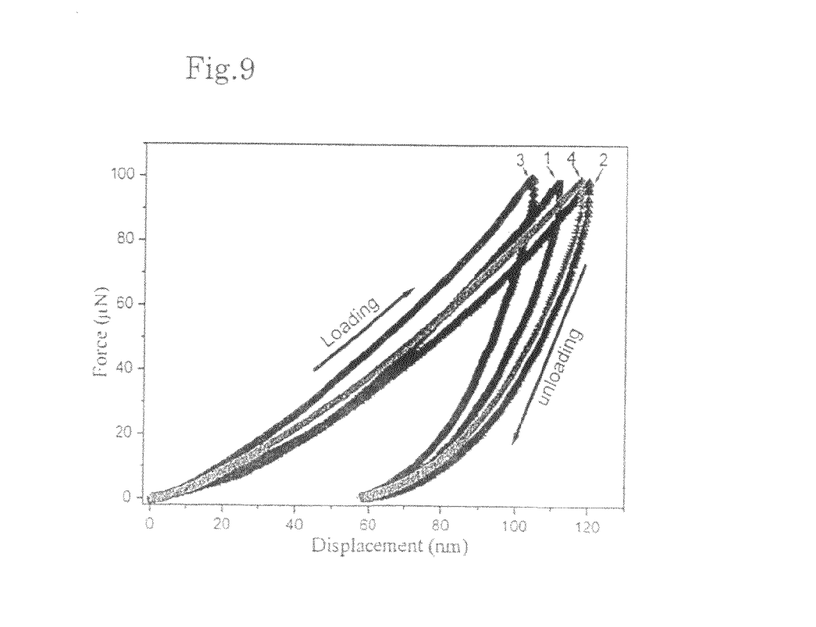
FIG. 9 Typical loading-unloading curves of ferritin and apoferritin films with and without cadmium nanostrands.

MEANING OF SYMBOL (In FIG. 9)
1: Apoferritin with nanostrands
2: Apoferritin without nanostrands
3: Ferritin with nanostrands
4: Ferritin without nanostrands

BEST MODE FOR CARRYING OUT THE INVENTION

Firstly, we explain a fabrication method for the free-standing ultrathin (nano) or thin protein membrane in detail. The invented fabrication method comprises the following steps as mentioned above.
(1) Step of formation of metal (Cd, Cu or Zn) hydroxide nanostrands;
(2) Step of obtaining composite nanofibers made of protein and the said metal hydroxide nanostrands;
(3) Step of filtration;
(4) Step of cross-linkage; and
(5) Step of removal of metal hydroxide nanostrands.

Though we are not needed to process in the above order, but the above order, namely (1)→(2)→(3)→(4)→(5), is most preferable.

Furthermore, we can add an additional step of peeling-off of composite nanofibers made of protein and the metal hydroxide nanostrands after (4) step of cross-linkage.

We can widely use various kinds of protein in this invention. Later we show examples using ferritin, apoferritin, cytochrome c, myoglobin and glucose oxidase (needless to say, the other protein can also be used). Mixed proteins can also be used as well as single protein, but single protein is preferable because we expect a good uniformity of membrane.

Figure 1:
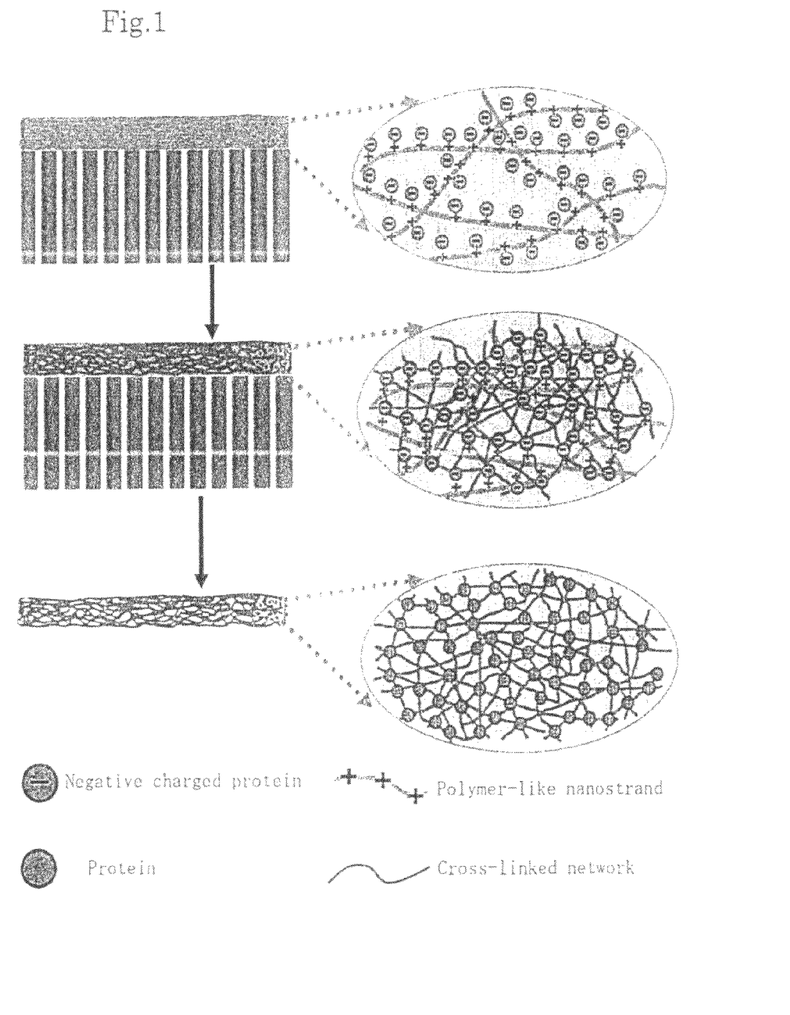
FIG. 1 Scheme of a typical fabrication process for the ultrathin (nano) or thin free-standing protein membrane.

A scheme of a typical fabrication process for the free-standing ultrathin (nano) or thin protein membrane was shown in FIG. 1.

In the initial step (i.e. formation of metal hydroxide nanostrands; not illustrated here), polymer-like positively charged metal hydroxide nanostrands are prepared as we described elsewhere (non-patent ref. 3, 4). Briefly, pH of a dilute Cd, Cu or Zn nitrate (otherwise, Cd or Zn chloride) solution is raised up to neutral or weak basic (pH=6.0-8.5) by adding a dilute alkali solution, and kept it at room temperature for several minutes to one day resulting in spontaneous formation of metal hydroxide nanostrands, whose diameter is ca. 2-3 nm and whose length reaches several tens of micrometers.

The obtained metal hydroxide nanostrands are mixed with negatively charged protein solution under stirring for defined hours, resulting in dispersion of composite nanofibers made of protein and the metal hydroxide nanostrands. The obtained dispersion is filtered on a filter such as polycarbonate (PC) membrane filter with 200 nm pores (porosity about 10%), forming composite nanofibrous films. Then, the films are treated with a solution of bifunctional cross-linkers (such as 10 wt % glutaraldehyde aqueous solution) for sufficient hours to complete cross-linkage reaction.

In case of using glutaraldehyde, the reaction is as followed.

Protein-NH$_2$+O=CHC$_3$H$_6$C=O→Protein-N=CHC$_3$H$_6$C=N-protein+2H$_2$O

We can also use other bifunctional cross-linkers, for example, various imidoesters, N-hydroxysuccinimide-esters or carbodiimides which are well known to be bifunctional cross-linkers of proteins, in substitution for glutaraldehyde.

In FIG. 1, an example that these cross-linked nanofibrous composite films are peeled off is shown. In order to peel off, we can immerse the above filter with films in alcohol (e.g. ethanol) resulting in forming cross-linked free-standing films.

Subsequently the above cross-linked free-standing films can be immersed in aqueous mineral acid such as HCl solution to remove the metal hydroxide nanostrands. Then the excess metal ions and HCl can be washed away using purified water. Thus we can obtain the pure (namely, not containing metal hydroxide) free-standing protein membranes floating in water. We can store these membranes in alcohol for further application and characterization.

The thickness of the protein membrane can be easily controlled from 10 nm to 10 μm by adjusting the volume of the filtering fibrous composite solution (see Example 3, Table 1).

In order to execute a rapid and simple separation (or condensation) of target materials, the thickness of the protein membrane is preferably 15 nm ~1000 nm, and more preferably 20 nm ~1000 nm. When a defined concentration of the fibrous composite are filtered, the thickness of the protein membrane and the time of the filtering process linearly depend on the filtering volume.

The diameter of the protein membrane is not limited, because the diameter of the film is basically determined by the inner diameter of the filtering funnel.

The above free-standing ultrathin or thin protein membrane has various applications. As described above, one application is a preparation of thin free-standing films composed of two layers, one of which is the above protein membrane, the other one is a thin molecular membrane which is formed by stacking defined molecules on the said protein membrane and cross-linking with bifunctional cross-linkers.

Here, as the defined molecules we can use various defined molecules such as synthetic macromolecules whose molecular weight is large enough not to go through the channels of the above protein membrane. We can use, for example, dendrimers having terminal NH$_2$ groups as the said synthetic macromolecules. Then, the dendrimers are preferably polyamidoamine whose molecular weight is over ca. 2,000 (large enough not to go through the channels of the above protein membrane).

EXAMPLES

Materials used in the following examples are followed. CdCl$_2$.2.5H$_2$O, Cu(NO$_3$)$_2$.3H$_2$-aminoethanol, Direct Yellow 50, Evans Blue, 8-aminonaphthalene-1,3,6-trisulfonic acid disodium salt, K$_3$[Fe(CN)$_6$], hydrogen chloride (5 M solution), glutaraldehyde (50 wt % aqueous solution) were purchased from Kanto Chemical. Tetrakis(1-methylpyridinium-4-yl) porphine p-Toluenesulfonate, 8-octanoyloxypyrene-1,3,6-trisulfonic acid trisodium salt, copper phthalocyanine tetrasulfonic acid tetrasodium salt, glucose oxidase, cytochrome c, myoglobin, horse spleen ferritin (76 mg/ml solution), and apoferritin (38 mg/ml solution) were purchased from Sigma-Aldrich. Deionized water (18.2 MΩ) was produced by a Millipore Direct-Q System, and used throughout the experiments. Polycarbonate (PC) membrane and filters (Nuclepore, Whatman) of 2.5 cm, 4.7 cm, and 9.0 cm in diameter were used for the preparation of free-standing films. Alumina membranes (Anodisc, pore size 0.2 μm, diameter 2.5 cm, thickness 60 μm) were also purchased from Whatman.

Instruments and methods used are followed. The films were characterized by using a scanning electron microscope (SEM, Hitachi S-4800), a transmission electron microscope (TEM, JEOL 1010), and a high-resolution transmission electron microscopy (HR-TEM, JEM 2100F) equipped with an energy-dispersive X-ray analysis system. The specimens for TEM and HR-TEM observation were prepared by transferring the free-standing film on a carbon-coated TEM grid. SEM observation was conducted after coating 2-nm thick platinum layer by using a Hitachi e-1030 ion sputter at the pressure of 10 Pa and the current density of 10 mA. UV-vis absorption spectra were obtained by using a SHIMAZU UV-3150 spectrophotometer. The photoluminescence spectra were obtained by a JASCO FP-6500 spectrofluorometer. The magnetic properties were measured using a commercial magnetometer with superconducting interference devise (MPMS-XL, Quantum Design). Mechanical properties were measured by using TriboIndenter (Hysitron Inc.), employing a diamond Berkovitch indenter with silicon substrate. The molecular dimensions estimated by a Chem3D ultra 10.0 (Cambridge Scientific Computing).

Example 1

Preparation and Characterization of the Invented Protein Membrane (a) Preparation In the initial step, polymer-like positively charged cadmium hydroxide nanostrands were prepared as we described elsewhere (non-patent ref. 2-4). Briefly, cadmium hydroxide nanostrands were prepared by quickly mixing a dilute NaOH or aminoethanol solution (2 mM, 20 mL) into 20 mL of 4 mM aqueous cadmium nitrate and stirring for a few minutes.

Protein (ferritin, apoferritin, cytochrome c, myoglobin, or glucose oxidase) was added into the above dispersion of cadmium hydroxide nanostrands and mixed under stirring for 30 mins. In the case of ferritin and apoferritin, the mixture was made of 1 ml, 3.8 mg/ml protein solution and 20 ml cadmium hydroxide nanostrand solution. In the case of cytochrome c, myoglobin, and glucose oxidase, 1 ml, 6.4 mg/ml protein solution mixed with 20 ml cadmium hydroxide nanostrand solution.

A certain volume of the mixture was filtered on polycarbonate membranes (diameters of membrane/funnel used for filtration: 3.2 cm) by suction filtering process under gauge pressure (ΔP) of 90 KPa. Then, the films were immersed into 10 wt % glutaraldehyde aqueous solution and cross linked for 1 hour at room temperature. These cross-linked nanofibrous composite films were peeled off by immersing PC membrane with films in ethanol. The resulting free-standing films were immersed in 10 mM HCl solution for 3 hrs to remove the inorganic nanostrands and then the excess cadmium ions and HCl were washed away using milli-Q water. Thus we obtained five kinds of pure free-standing protein (ferritin, apoferritin, cytochrome c, myoglobin, and glucose oxidase) membranes floating in water respectively.

(b) Characterization

Figure 2:
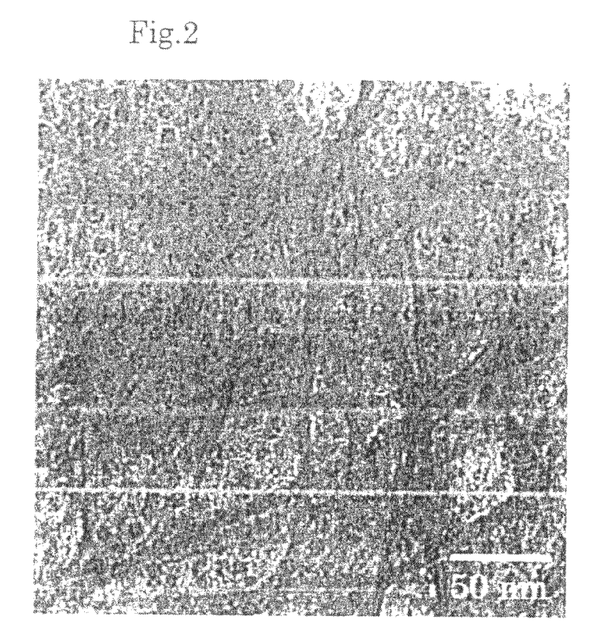
FIG. 2 Top view TEM image of the ferritin/cadmium hydroxide nanostrands nanofibrous film after cross-linkage.

FIG. 2 is TEM image of the ferritin/cadmium hydroxide nanostrands nanofibrous film after cross-linkage and this clearly shows that fibrous structures and the proteins almost assembled along the nanostrands. In this image, the ferritin proteins appear as black dots with diameter about 8 nm due to the iron compound cores of ferritin. The cadmium hydroxide nanostrands appear as about 2 nm fiber structures.

Figure 3:
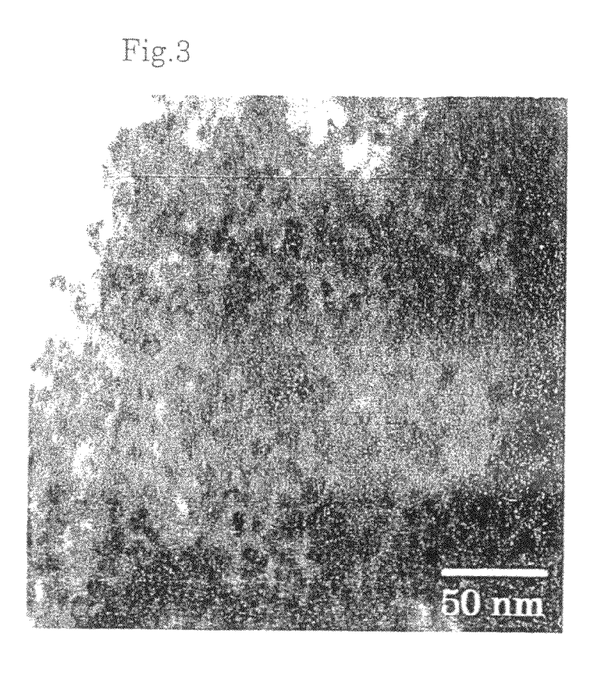
FIG. 3 Top view TEM image of the ferritin membrane after removal of cadmium hydroxide nanostrands from the ferritin/cadmium hydroxide nanostrands nanofibrous film shown in FIG. 2.

FIG. 3 is TEM image of the pure ferritin membrane after removal of metal hydroxide nanostrands from the ferritin/cadmium hydroxide nanostrands nanofibrous film shown in FIG. 2, and this shows that the fibrous structures were disappeared, which means that the nanostrands were completely removed.

Figure 4:
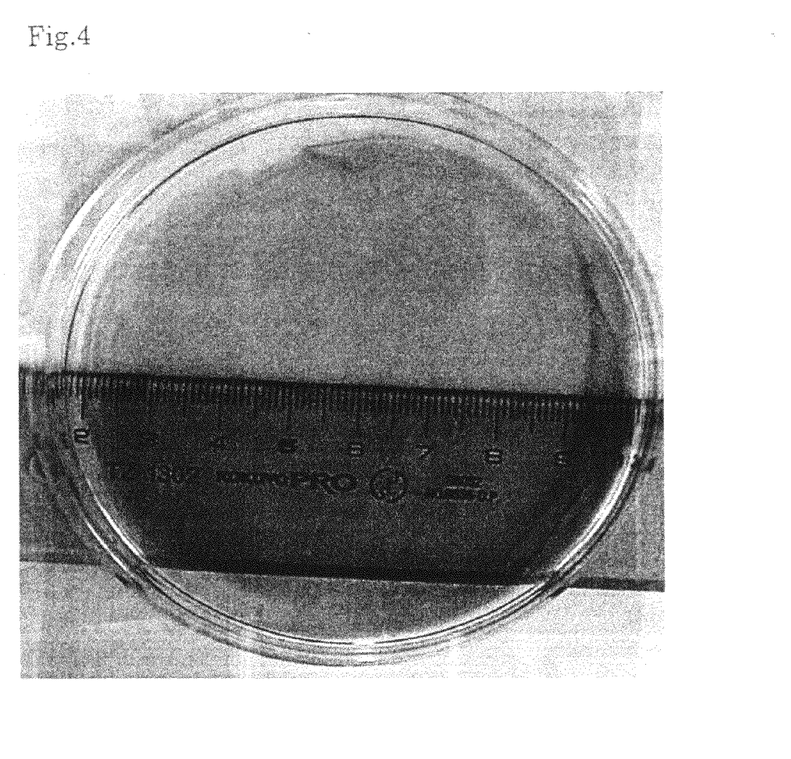
FIG. 4 Copy of a photograph of a free-standing ferritin membrane with a diameter of 7.5 cm.

FIG. 4 shows a copy of the photograph of a representative free-standing ferritin membrane with diameters of 7.5 cm. The diameter of the membrane is equal to the size of the funnel using for filtration.

The morphology and composition of the film before and after removal of cadmium hydroxide nanostrands were further examined in detail by using SEM and EDX. Free-standing films were transferred onto anodic alumina membranes with pore size 200 nm.

Figure 5:
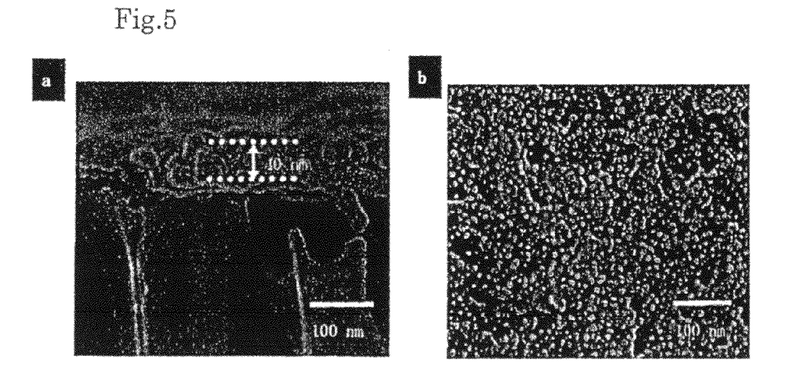
FIG. 5 Cross-sectional SEM image of ferritin/cadmium hydroxide nanostrands film (thickness: 40 nm) before removal of cadmium hydroxide nanostrands.
Figure 6:
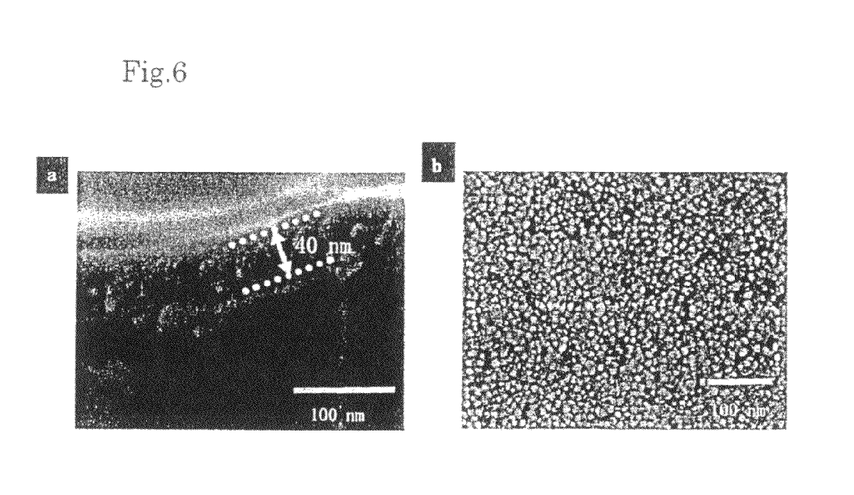
FIG. 6 Cross-sectional SEM image of ferritin membrane (thickness: 40 nm) after removal of cadmium hydroxide nanostrands.

FIG. 5 shows (a) cross-sectional and (b) top view SEM image of ferritin/cadmium hydroxide nanostrands film (thickness: 40 nm) before removal of cadmium hydroxide nanostrands, and FIG. 6 shows (a) cross-sectional and (b) top view SEM image of ferritin membrane (thickness: 40 nm) after removal of cadmium hydroxide nanostrands.

Comparing FIG. 5a and FIG. 6a, the thickness of the films didn't show big difference, namely, there was almost no decrease of thickness after removal of nanostrands. This means that there is no collapse due to the removal of nanostrands. But the surface of the film after removal of nanostrands becomes smoother than that of before removal of nanostrands (compare FIG. 5b and FIG. 6b).

Figure 7:
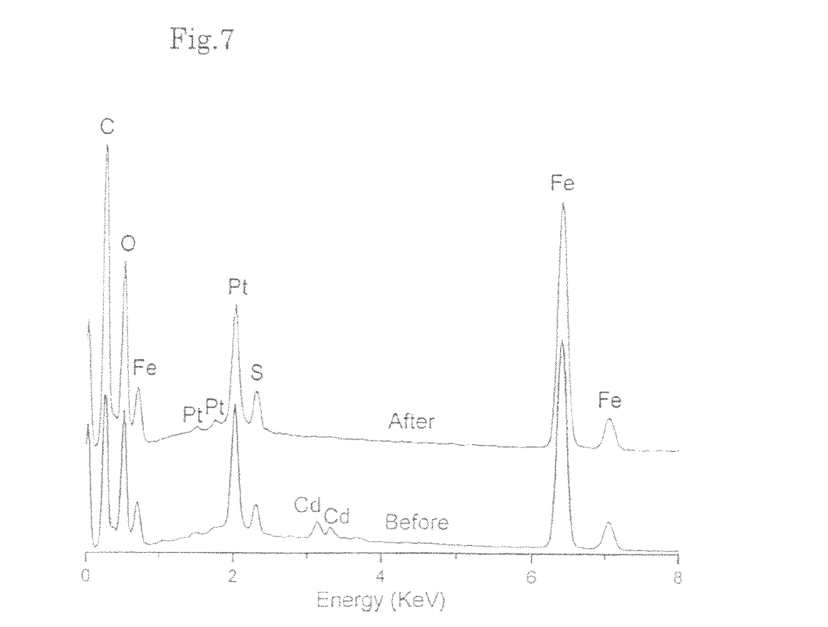
FIG. 7 EDX spectra recorded from the cross-linked film before and after removal of cadmium hydroxide nanostrands.
Figure 8:
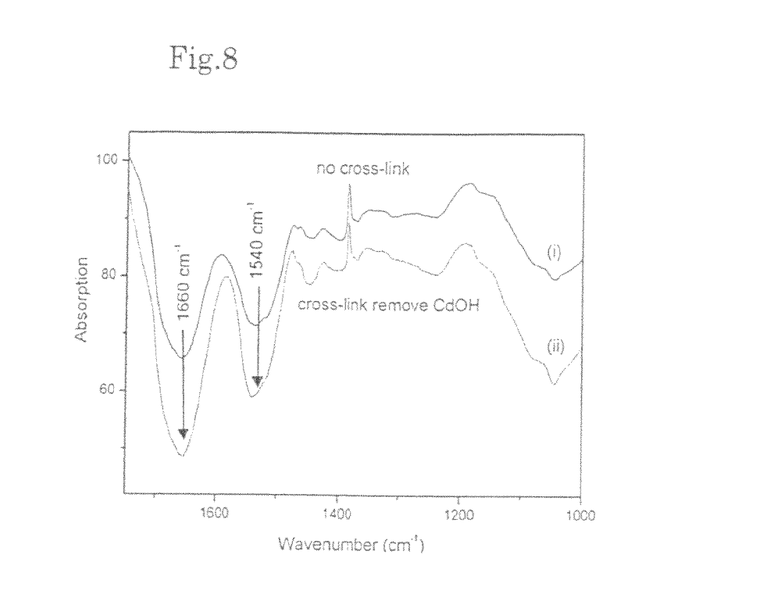
FIG. 8 FTIR spectra of the film of (i) before cross-linkage and (ii) after cross-linkage followed by removal of cadmium hydroxide nanostrands.

FIG. 7 shows EDX spectra recorded from the cross-linked film before and after removal of cadmium hydroxide nanostrands. These EDX spectra confirmed that the cadmium element was completely removed away from the film which is consistent with the above TEM investigations. The FTIR spectra of native ferritin (no cross-linkage) and the obtained pure ferritin membrane were shown in FIG. 8. The characteristic peaks are almost the same, just the intensity of the peaks of ferritin membrane are stronger than that of native ferritin. The same position of peaks is because no any new functional group was introduced into the membrane during cross-linking process. The increasing of the intensity of the peaks at about 1660 cm$^{-1}$ is originated from C=N covalent bond formation during the cross-linking process (Rozkiewicz, D. I. et al, *Chem. Eur. J.* 12, 6290-6297, 2006). These results indicate that the protein is not denatured.

Additionally, even though cadmium hydroxide nanostrands do not affect the protein membrane due to removal of them, the other more safe nanostrands, such as copper hydroxide nanostrands and zinc hydroxide nanostrands with similar properties to that of cadmium hydroxide nanostrands, were also used successfully to prepare free-standing protein membranes (data were not shown here).

Example 2

Controlled Synthesis of Different Thickness and Diameter Protein Membrane (a) Preparation We prepared ultrathin free-standing pure protein membranes similarly to Example 1 except that the time of the filtering process and/or the filtering volume were varied and that diameters of membrane/funnel used for filtration were 1.7 cm, 3.2 cm and 7.5 cm. The results were shown in Table 1.

TABLE 1

| Protein | No. | $V_{mixture}{}^a$ (ml) | Process time (min) | Diameter (cm) | Thickness (nm) | Error (nm) |
|---|---|---|---|---|---|---|
| Ferritin | 1 | 0.25 | 0.5 | 1.7 | 40 | ±2 |
|  | 2 | 0.375 | 0.75 | 1.7 | 60 | ±2 |
|  | 3 | 0.65 | 1.2 | 1.7 | 105 | ±5 |
|  | 4 | 1.25 | 3 | 1.7 | 200 | ±5 |
|  | 5 | 3.75 | 8 | 1.7 | 600 | ±10 |
|  | 6 | 10 | 20 | 1.7 | 1,550 | ±20 |
|  | 7 | 25 | 60 | 1.7 | 4,000 | ±50 |
|  | 8 | 1.7 | 1.2 | 3.2 | 60 | ±2 |
|  | 9 | 9 | 10 | 3.2 | 300 | ±10 |
|  | 10 | 9 | 1 | 7.5 | 60 | ±2 |
| Apoferritin | 11 | 10 | 11 | 3.2 | 300 | ±10 |
|  | 12 | 3.5 | 0.5 | 7.5 | 25 | ±2 |
|  | 13 | 7 | 1 | 7.5 | 45 | ±2 |
|  | 14 | 20 | 3 | 7.5 | 140 | ±5 |
| Myoglobin | 15 | 0.25 | 0.5 | 1.7 | 50 | ±2 |
| Cyt. c | 16 | 0.3 | 0.5 | 1.7 | 50 | ±2 |
| GOx | 17 | 0.3 | 0.5 | 1.7 | 50 | ±2 |

Here, $V_{mixture}{}^a$ is the volume of the filtered mixture, which was made of 2 ml, 3.8 mg/ml of ferritin or apoferritin protein (or 6.4 mg/ml of other protein) solution and 40 ml cadmium hydroxide nanostrands solution. The thickness of protein membrane was measured from the cross-section SEM images.

(b) Characterization

The films were characterized by SEM images and TEM images (not shown here) as well as by naked eye's observation (or photographs). From these results we can see that the thickness of the protein membrane and the time of the filtering process linearly depend on the filtering volume. In these examples, thin films were synthesized in three diameters, 1.7 cm, 3.2 cm and 7.5 cm. And we also found for ferritin, the thinnest thickness is 40 nm for 1.7 cm, but which is 60 nm for 3.2 and 7.5 cm, respectively. The thickest one can be reach up to 4000 nm for 1.7 cm with one hour filtering time. Namely, in case of ferritin the thickness of ferritin films can be controlled in the range from 40 nm to 4,000 nm.

Comparing the example 60 nm, 200 nm and 600 nm, and 4000 nm thick films before removal of cadmium nanostrands, the thicker the film, the deeper the color was. The thicknesses of the films of corresponding protein films after removal of cadmium hydroxide nanostrands were almost not changed. This indicates that the films were not clasped after removal of nanostrands, resulting more porous films.

In case of another protein, apoferritin, the obtained apoferritin ultrathin protein membranes showed the films with homogenous thickness of 25 nm, even in the case of 7.5 cm diameter (No. 12). The ratio of diameter to thickness is up to 3,000,000. TEM image (not shown here) indicates the film is very flexible in nanometer scale. The extremely macroscale flexibility was confirmed by the aspiration of this 7.5 cm diameters apoferritin free-standing membranes into a pipette tip with diameter of 0.8 mm. The protein membranes surprisingly could reversibly pass through a holes 8,790 times smaller than its own area. This is due to its flexible and extreme thinness.

The mechanical properties of ferritin and apoferritin films with thickness 1550 nm before and after removal of cadmium hydroxide nanostrands were measured by nanoindentation using TriboIndenter (Hysitron Inc.), employing a diamond Berkovitch indenter, respectively. The typical load-unload curves for them were shown in FIG. 9. For each sample, three points were measured and giving the average data. The hardness, H, and Young's modules were shown in Table 2.

TABLE 2

Mechanical properties of ferritin and apoferritin films

| Sample | E. Young's module (GPa)[a] | | | | Hardness (MPa) | | | |
|---|---|---|---|---|---|---|---|---|
| | n1[b] | n2 | n3 | Avg.[c] | n1 | n2 | n3 | Avg. |
| Ferritin (before)[d] | 5.97 | 6.20 | 6.25 | 6.14 | 378 | 386 | 391 | 385 |
| Ferritin (after)[e] | 4.29 | 4.41 | 4.63 | 4.44 | 327 | 326 | 313 | 322 |
| Apo-ferritin (before) | 4.49 | 5.06 | 4.75 | 4.77 | 316 | 349 | 315 | 327 |
| Apo-ferritin (after) | 4.43 | 4.69 | 4.64 | 4.58 | 312 | 310 | 308 | 310 |

[a]the value of Poisson ration is 0.5 and used for calculating the Young's module.
[b]n1 means the measurement point number. n1, n2 and n3, means three points are measured.
[c]Avg means average value of that measured from three points.
[d](before) means before removing cadmium hydroxide nanostrands.
[e](after) means after removing cadmium hydroxide nanostrands.

It can be concluded that hardness and the Young's modules of films before removal of nanostrands are larger than that of the films after removal of nanostrands. At the same time, the hardness and Young's modules of ferritin films are larger than that of apoferritin. The difference among the films before and after removal of nanostrands shows that the enhanced mechanical properties of the protein films are originated from interaction between the inorganic components and protein. At the same time, the iron compound in ferritin makes the ferritin film with larger value of hardness and Young's modules than that of apoferritin film. These values of the hardness and the Young's modules of ferritin and apoferritin films are ten times larger than that reported of glyoxal cross-linked native protein films, such as gelatin, soy, casein and sodium caseinate (Vaz, C. M. et al, *J. Mater. Sci.: Mater. in Medicine* 14, 789-796, 2003), and 4 times as that of glutaraldehyde cross-linked soy protein films (Chabba, S. et al, *J. Mater. Sci.* 40, 6263-6273, 2005).

We additionally did an experiment that a 60 nm thick film was sealed on a plastic tube hole with diameter inner 5 mm and outer diameter 7 mm, then connected with another plastic tube with inner diameter 7 mm and outer diameter 10 mm, and then ethanol solution of directly yellow was carefully filled into the large tube and hold it vertically. It was found that such film can support a column of ethanol of 21.5 cm (it was calculated that about 180,000 times heavier than its own weight was supported without apparent permeation of ethanol).

When the nanostrands were removed from the ferritin or apoferritin film, the film becomes more flexible as seen by naked eye observation of films with 1550 nm thick (photographs not shown). This phenomenon is in agreement with the mechanical properties before and after remove nanostrands. These protein films after removal of nanostrands are very stable under both acid and basic conditions, as well as for organic solvent solution, such as acetone, benzene and chloroform, which are desirable for application.

Example 3

Application of the Invented Protein Membrane to Separation, Condensation, Absorption or Desorption The separation performance of these free-standing ultrathin pure protein membranes were investigated by studying the permeation of molecules with different size, charge states, and pH. The filtration process was carried out under 90 kPa pressure. The volume of the molecules is kept as 20 ml. The flux rate is equal to the permeated volume divided by the valid area and the processing time. The permeation performance was monitored by the UV-Vis absorption spectra recorded on the solution before and after filtration, and also the upper solution. The results were summarized in Table 3.

TABLE 3

The separation performance of different molecules at different pH through a 60 nm thin free-standing ferritin membranes

| Molecules (mw) | C (µM) | pH | L × W[a] (Å$^2$) | Molecule-Charging | Ferritin-charging | Permeation (%) | Flux rate Lm$^{-2}$h$^{-1}$ |
|---|---|---|---|---|---|---|---|
| ANTS (650.58) | 40 | 6.27 | 8.2 × 7.0 | − | − | 99.86 | 7639.4 |
| | | 1.53 | | − | + | 98.75 | 7370.3 |
| | | 13.3 | | − | − | 99.67 | 9167.3 |
| [Fe(CN)$_6$]$^{3−}$ (212) | 1000 | 6.25 | 8.7 × 8.7 | − | − | 99.63 | 7545.6 |
| EB (960.81) | 10 | 6.41 | 28.5 × 7.8 | − | − | 27.98 | 7065.6 |
| | | 13.1 | | − | − | 99.54 | 8653.4 |
| PC/Cu (984.25) | 2 | 1.44 | 18.6 × 13.4 | − | + | 0.09 | 6374.3 |
| | | 13.01 | | − | − | 0.14 | 8356.4 |
| | | 6.75 | | − | − | 0.1 | 6945.2 |
| TMPyP (1,363.6) | 1.5 | 6.32 | 18.2 × 13.2 | + | − | 0.15 | 6354.7 |
| Cyc. c (13,000) | 2 mg/ml | 6.39 | 2.5 × 2.5 × 3.7 | + | − | 0.06 | 6276.9 |
| | | 11.02 | | − | − | 0.04 | 6512.4 |
| DY (956.82) | 10 | 1.66 | 29.3 × 8.1 | − | + | 0.55 | 5372.4 |
| | | 2.71 | | − | + | 0.81 | 5382.6 |
| | | 3.19 | | − | + | 0.95 | 5364.2 |
| | | 3.83 | | − | + | 25.13 | 5400.2 |
| | | 4.31 | | − | + | 25.38 | 6122.3 |
| | | 6.19 | | − | − | 33.51 | 6178.5 |
| | | 7.09 | | − | − | 99.32 | 7258.9 |
| | | 9.53 | | − | − | 99.53 | 7268.4 |
| | | 12.11 | | − | − | 99.12 | 7350.3 |
| | | 12.96 | | − | − | 99.96 | 8767.5 |

TABLE 3-continued

The separation performance of different molecules at different pH through a 60 nm thin free-standing ferritin membranes

| Molecules (mw) | C (μM) | pH | L × W$^a$ (Å$^2$) | Molecule-Charging | Ferritin-charging | Permeation (%) | Flux rate Lm$^{-2}$h$^{-1}$ |
|---|---|---|---|---|---|---|---|
| DY/(PC/Cu) | 10/2 | 6.35 | 29.3 × 8.1/ | – | – | 43.51/ 0.05 | 6985.1 |
|  |  | 13.12 | 1.61 × 1.61 | – | – | 99.45/ 0.04 | 8546.7 |

High performance size-based selective molecular separation was achieved by using a 60 nm thin, ferritin film with diameter of 1.7 cm. Big molecules, such as PC/Cu (MW: 984.25), TMPyP dye (MW: 1,363.6) and Cyt. c (MW: 13,000) were completely separated from their aqueous solutions. ANTS molecules (MW: 650.58) and [Fe(CN)$_6$]$^{3+}$ ions (MW: 212) completely went through such film. DY (direct yellow 50) (MW: 956.82), and EB (Evans blue) (MW: 960.81) molecules partially permeated through it at neutral pH. However, by changing the pH of DY or EB solutions, these dye molecules completely went through the protein membrane at pH higher than 7 and were forbidden to pass at pH lower than 3.19. These pH dependent performances are due to the surface charge property of the protein. In the case for ferritin and apoferritin, the isoelectric points of them are the same at about pH 4.4. So, when the pH of dye solution is lower than 4.4, the membrane is positively charged, and adsorbs the negatively charged dye molecules through electrostatic interaction, and makes the channels smaller. If the dye molecules are smaller enough, such as ANTS molecules, 8.23×7.0×3.17 Å$^3$ and [Fe(CN)$_6$]$^{3-}$, 8.7×8.7×8.7 Å$^3$, they still can go through the smaller channels. However, if the molecule size is bigger than these smaller channels, it can not pass through the film. Of cause, if the dye molecules are bigger than the channels, at any pH, it can not go through the film. At pH 13.03, the permeation of the mixture solution of PC/Cu and DY molecules shows that DY thoroughly permeates through the film, but PC/Cu were almost can't pass through it. However, all the flux rates of water are more than 5,000 Lm$^{-2}$ h$^{-1}$ under pressure of 90 kPa. Due to no permeation of the bigger molecules, they can be concentrated from their diluted solution.

Figure 10:
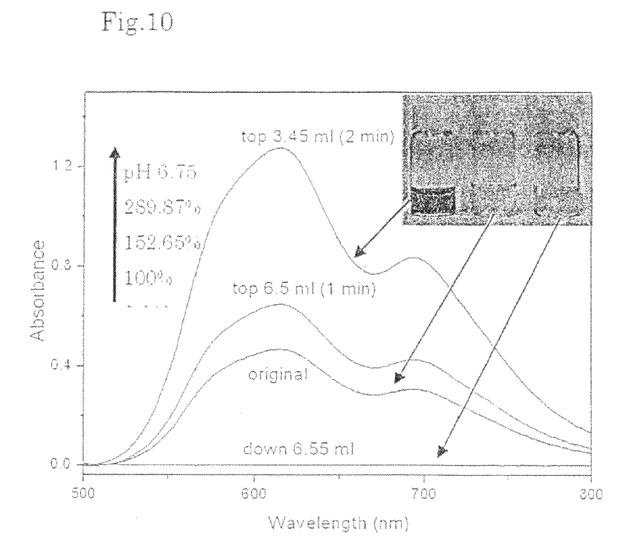
FIG. 10 Typical UV-visible spectra and copies of photographs showing concentration performance for PC/Cu.

For example, PC/Cu molecules solution was examined (FIG. 10). PC/Cu molecules could be efficiently concentrated from 10 μM solution to 28.89 μM within 2 min by using a 60 nm thick ferritin membrane on alumina membrane by suck filtration under 90 kPa. UV-vis spectra were used to monitor the efficiency of the concentration performance. Increasing the process time, the upper solution become more and more blue, but there is no detectable PC/Cu in the filtration solution. The flux rate is 6671.9 L-m$^{-2}$ h$^{-1}$.

The reversible charged properties of the proteins, when the pH is higher or lower than its isoelectric point, they can be used as an absorber for the charged molecules or particles in solution with different pH, and then release them into the other solution by changing the pH. For this study, the reversible absorption and desorption of dye molecules (Evans blue and DY) were investigated. 300 nm thick and 3.2 cm diameter apoferritin membrane was used for adsorption and desorption of Evans blue molecules in solution by controlling the pH of the solution. The dye molecules in 10 ml, 10 μM, Evans blue solution at pH 1.50 can be completely captured by the protein membrane within 1 day. And these captured molecules can be further released in basic solution such as pH 13.09 water. The capturing and releasing process were monitored by Uv-vis spectroscopy.

Figure 11:
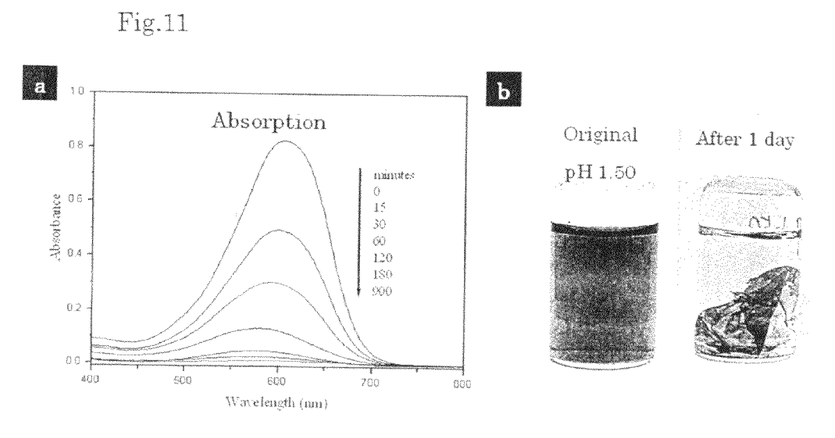
FIG. 11 Typical UV-visible spectra and copies of photographs showing absorption of Evans Blue by using apoferritin membrane (300 nm thick, 3.2 cm diameter).
Figure 12:
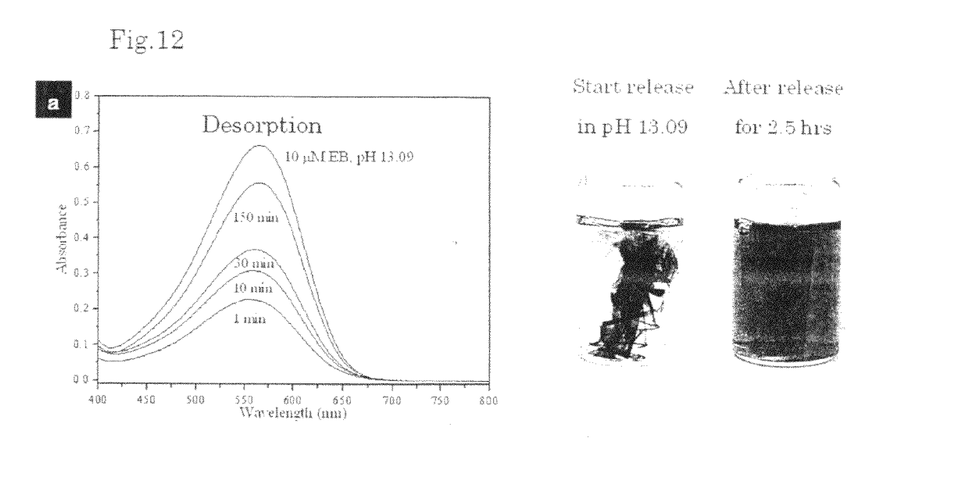
FIG. 12 Typical UV-visible spectra and copies of photographs showing desorption of Evans Blue by using apoferritin membrane (300 nm thick, 3.2 cm diameter).

FIG. 11a shows typical UV-visible spectra recorded during the capturing process with increasing time. FIG. 11b, copies of photographs of original and after one day, clearly show that the dye molecules were completely removed from the solution by the membrane and this was consistent with the Uv-vis result. The releasing performance was shown in FIG. 12a and FIG. 12b. After 2.5 hrs, 83.5% of Evans blue molecules were released from the membrane into the solution. The longer the time, the more amount dye molecules was released into the solution. The maximum rate of the first released circle is 94.5% similar to that of DY molecules (data not shown). But, after the first capture and releasing circle, the release efficiency is 99.4% for the later circles. The capture and release process is due to the pH triggering the charge properties of the apoferritin membrane. When the pH of the solution is lower than that isoelectric of apoferritin pH 4.4, the membrane will be positively charged, contrary, if the pH higher than 4.4, the protein membrane will be negatively charged. Therefore, in the pH of the solution lower than 4.4, negatively charged molecules will be trapped into the membrane through electrostatic interaction, otherwise, the negatively charged dye molecules will be push away from the membrane due to the repulsion force. The blue color (FIG. 11) and purple color color (FIG. 12) of the Evans blue solution with pH 1.50 and 13.09, respectively is due to the dye molecules itself.

Figure 13:
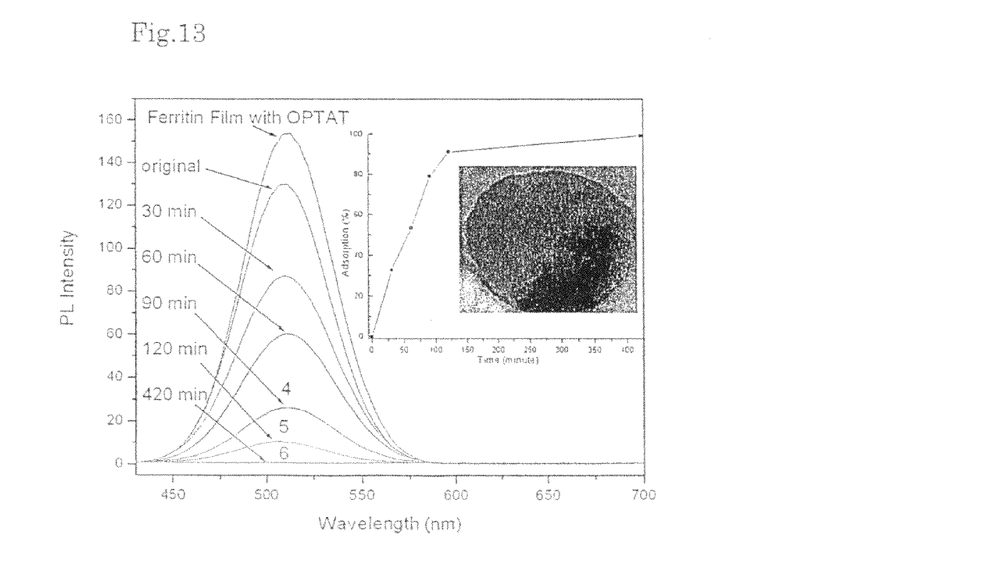
FIG. 13 Typical photoluminescence spectra showing that the fluorescent dye molecules adsorbed by ferritin membrane. The inset photograph (copy) was taken under irradiated with 375 nm light. The molecular structure was shown in the down inset.

Another example for the adsorption performance was shown in FIG. 13. Fluorescent dye, 8-octanoyloxypyrene-1,3,6-trisulfonic acid trisodium salt (OPTAT), 10 μM, 10 ml solution with pH 1.39, were adsorbed by 300 nm thick, 3.2 cm diameter, ferritin membrane. The photoluminescence (PL) spectra show that after 7 hours, all the molecules were trapped into the ferritin membrane, and the film showed stronger emission than that of the original solution. The inset photo was obtained by exciting the membrane at 375 nm.

Example 4

Another application of the invented protein membrane to preparation of thin free-standing films composed of two layers, the one layer is the protein membrane, the other layer is a thin molecular membrane formed on it.

(a) Preparation of protein (apoferritin) films: the process of preparation of protein (apoferritin) films was the same as described in the Example 1.

Figure 14:
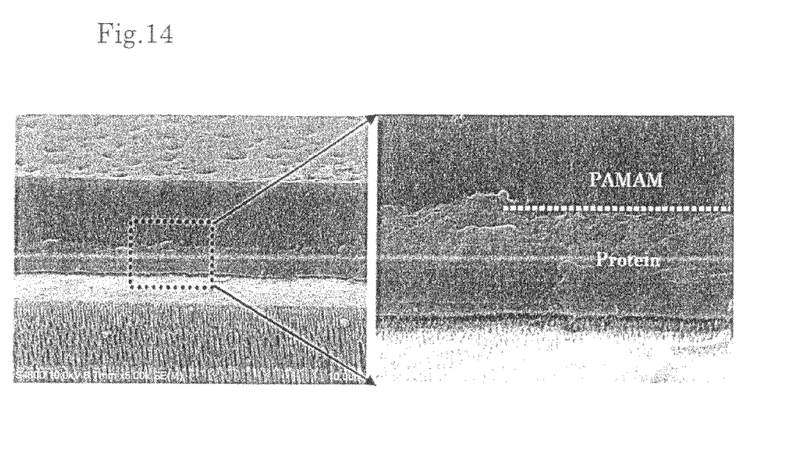
FIG. 14 Typical SEM images of a PAMAM membrane (thickness: 4.6 micrometer) formed on a apoferritin membrane (thickness: 1.9 micrometer) surface. (b) shows magnified image of parts surrounded by dotted line in (a).

(b) Preparation of thin free-standing films composed of two layers, the one layer is the protein (apoferritin) membrane, the other layer is a thin molecular membrane formed on the protein (apoferritin) membrane surface A 1.9 micrometer thin apoferritin membrane mounted on a polycarbonate membrane with pore size of 200 nm was used in a suction filtration system as filter. 2 ml, 0.2 wt % dendrimer, PAMAM (Polyamidoamine) molecule (general 4, molecular weight: 14215, diameter: 4.5 nm, surface —NH$_2$ groups: 64, purchased from Sigma-Aldrich) methanol solution was filtered on the above system under 90 kPa pressure. After filtering away methanol, PAMAM molecule filter cake was cross-linked by 1 ml, 5 wt % glutaraldehyde for 1.5 hrs. Finally, the film was washed by methanol and water four times. FIG. 14 shows typical SEM images of a 4.6 micrometer thick PAMAM film formed on a 1.9 micrometer thick apoferritin film surface.

The thickness of the PAMAM film can be controlled by the filtering volume of PAMAM solution.

Additionally other molecular films also can be prepared by using the same filtering and cross-linking process based on protein membranes. This method provides a simple way to build functional thin molecular films for various applications, such as separation.

What we claim is:

1. A fabrication method for a flexible porous free-standing protein membrane formed by cross-linked protein, comprising:
   (1) a first step of mixing metal hydroxide nanostrands and protein to obtain a composite made of the protein and the metal hydroxide nanostrands;
   (2) a second step of forming a membranous body formed by said composite made of the protein and the metal hydroxide nanostrands, and mutually cross-linking said protein by a bifunctional cross-linker; and
   (3) a third step of dissolving and removing said metal hydroxide nanostrands whose diameters are 2-3 nm to produce a flexible porous free-standing protein membrane containing channels,
   wherein a thickness of the flexible porous free-standing protein membrane is 10 μm or less.

2. The fabrication method according to claim 1, wherein said membranous body is formed by assembling composite nanofibers made of the protein and said metal hydroxide nanostrands.

3. The fabrication method according to claim 1, wherein metal hydroxide of the metal hydroxide nanostrands is one selected from the group consisting of Cd, Cu, and Zn.

4. The fabrication method according to claim 1, wherein the bifunctional cross-linker is one selected from the group consisting of glutaraldehyde, N-hydroxysuccinimide-ester, and carbodiimide.

5. The fabrication method according to claim 1, further comprising mixing the metal hydroxide nanostrands with negatively charged protein solution for a predetermined time thereby obtaining composite nanofibers made of the protein and the metal hydroxide nanostrands.

6. The fabrication method according to claim 5, further comprising filtering the metal hydroxide nanostrands prior to the forming of the membranous body.

7. The fabrication method according to claim 6, further comprising adjusting a volume of the filtering of the metal hydroxide nanostrands thereby obtaining the porous membrane having the thickness of 10 μm or less.

8. The fabrication method according to claim 1, wherein a length of the metal hydroxide nanostrands is several tens of micrometers.

* * * * *